(12) United States Patent
Willis et al.

(10) Patent No.: US 8,088,107 B1
(45) Date of Patent: Jan. 3, 2012

(54) HEMODIALYSIS NEEDLE AND METHOD FOR INSERTING THE SAME

(76) Inventors: Frank Willis, Woodbury, NJ (US); Kevin Barber, Millville, NJ (US)

( * ) Notice: Subject to any disclaimer, the term of this patent is extended or adjusted under 35 U.S.C. 154(b) by 676 days.

(21) Appl. No.: 12/077,093

(22) Filed: Mar. 17, 2008

(51) Int. Cl.
*A61M 5/178* (2006.01)
*A61M 37/00* (2006.01)

(52) U.S. Cl. .................................. 604/164.12; 604/507

(58) Field of Classification Search .............. 604/110, 604/164.01, 164.08, 164.09, 164.11, 164.12, 604/165.01–165.03, 177, 507
See application file for complete search history.

(56) References Cited

U.S. PATENT DOCUMENTS

| | | | | |
|---|---|---|---|---|
| 4,349,022 A | * | 9/1982 | Ishikawa | 604/180 |
| 5,242,427 A | * | 9/1993 | Bilweis | 604/264 |
| 5,342,382 A | * | 8/1994 | Brinkerhoff et al. | 606/184 |
| 5,571,134 A | * | 11/1996 | Yoon | 606/185 |
| 5,649,911 A | | 7/1997 | Trerotola | |
| 6,015,401 A | | 1/2000 | Brackett et al. | |
| 7,022,110 B2 | | 4/2006 | Shibata | |
| 2005/0080397 A1 | | 4/2005 | Altman | |
| 2005/0145677 A1 | | 7/2005 | Ooyauchi et al. | |
| 2005/0149117 A1 | * | 7/2005 | Khosravi et al. | 606/215 |
| 2006/0270988 A1 | | 11/2006 | Valaie | |

* cited by examiner

*Primary Examiner* — Nicholas Lucchesi
*Assistant Examiner* — Nathan R Price
(74) *Attorney, Agent, or Firm* — Norman E. Lehrer

(57) ABSTRACT

A hemodialysis needle assembly and system that includes a first outer needle having a conical tip and a sidewall where the sidewall has a plurality of apertures located adjacent the tip, a second introducer needle located within the outer needle, a guide wire located within the introducer needle, and a spring motor removably secured to the outer needle. The introducer needle and the guide wire are inserted into a patient's vein and the spring motor releases the outer needle into the vein after the introducer needle and the guide wire are properly placed within the patient. The introducer needle, the guide wire, and the spring motor are removed from the patient after the outer needle is in place within the vein.

6 Claims, 2 Drawing Sheets

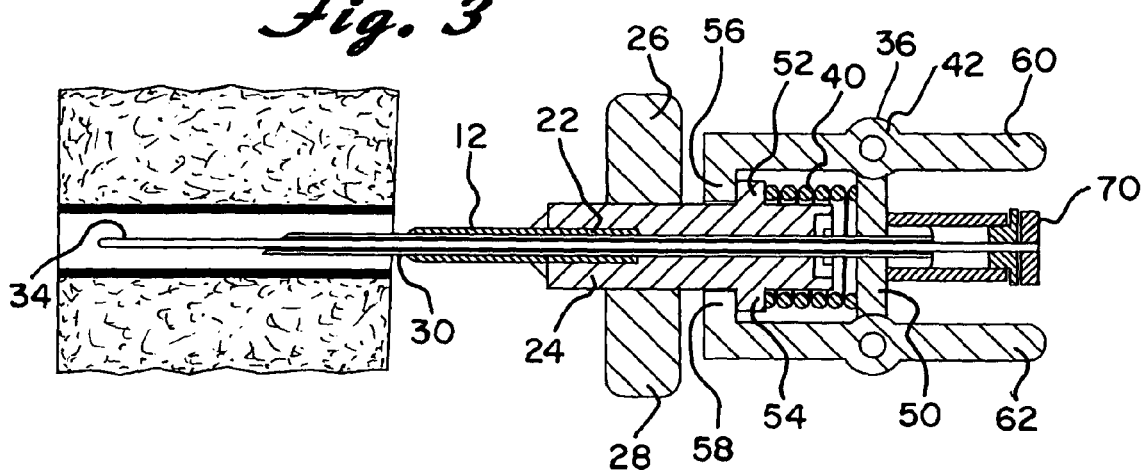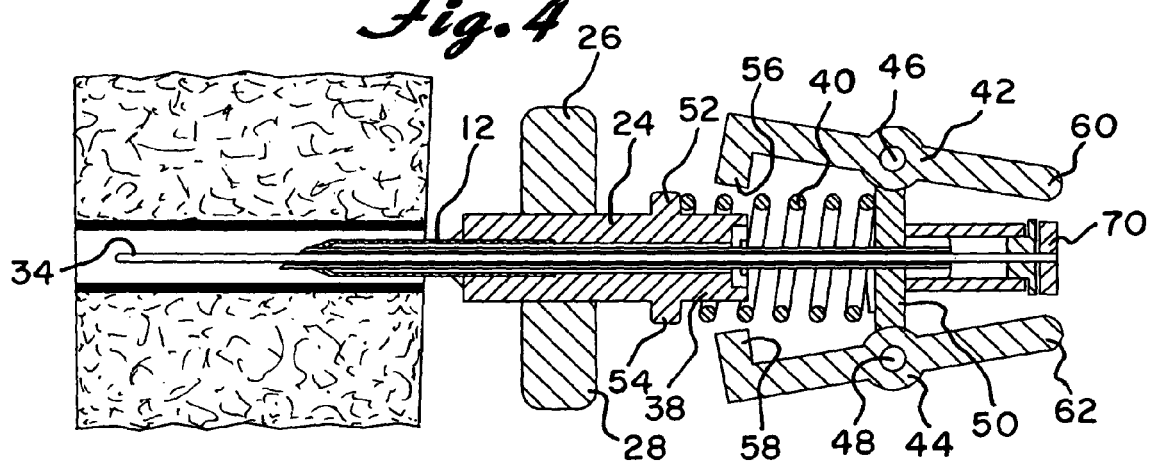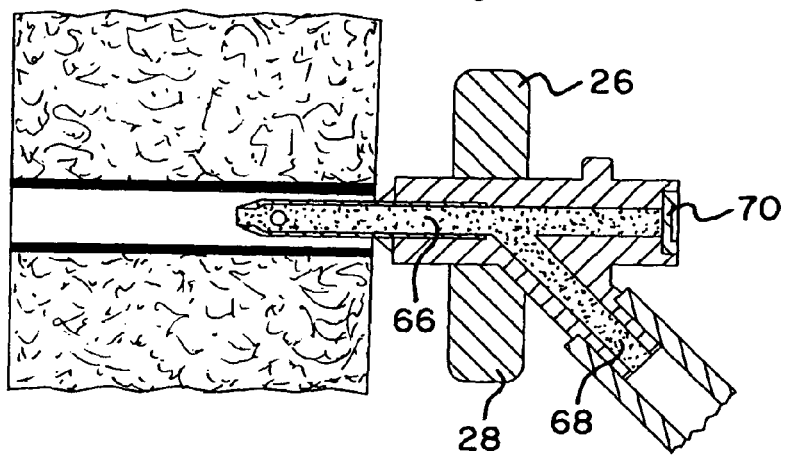

HEMODIALYSIS NEEDLE AND METHOD FOR INSERTING THE SAME

BACKGROUND OF THE INVENTION

The present invention is directed toward a hemodialysis needle and more particularly toward a needle that allows more comfort for the patient.

Dialysis is a well known treatment for end stage renal disease. Typically a patient sits in a hemodialysis chair and has two needles inserted into a vascular access in a patient's arm in order to draw blood out of the body through a blood circuit. A patient must undergo this treatment two to three times a week.

Conventionally, in the United States, dialysis needles are single large number 15 to number 17 gauge with an angular cut to make a point. The edges of this angular cut are razor sharp and often cut the edge of the penetration hole which can cause excessive bleeding. Introducer "double" type needles do exist but their use does not improve dialysis Blood is drawn through the needle and into a dialysis machine where the blood is filtered of toxins and waste products and is then returned to the body. The procedure is often painful and quite lengthy.

Many hemodialysis treatments are known. For example, U.S. Pat. No. 7,022,110 to Shibata discloses a hemodialysis needle that includes a large outer needle with a tapered conical tip and an inner introducer needle located within the outer needle. The inner needle may be removed once the outer needle is in place.

Published U.S. Patent Application No. 2005/0080397 to Altman discloses a dialysis needle/catheter system where the needle penetrates a patient's vein and then the catheter is inserted therein. However, this system does not appear to be less traumatic or painful to a patient.

A need exists for a hemodialysis treatment that is effective yet causes less pain and more comfort for the patient.

SUMMARY OF THE INVENTION

The present invention is designed to overcome the deficiencies of the prior art discussed above. It is an object of the present invention to provide a hemodialysis needle that allows more comfort for the patient and less difficulty for the technicians or other medical personnel.

It is another object of the present invention to provide a hemodialysis needle that is efficient and less traumatic than dialysis systems that are currently known.

Another object of the present invention is that this needle will resist infiltrations, at insertion, which is when the needle goes outside the wall of the vein. Also the increased peripheral radial blood flow tends to center the needle pushing the vein wall away from the wall of the needle.

In accordance with the illustrative embodiments demonstrating features and advantages of the present invention, there is provided a hemodialysis needle assembly and system that includes a first outer needle having a conical tip and a sidewall where the sidewall has a plurality of apertures located adjacent the tip, a second introducer needle located within the outer needle, a guide wire located within the introducer needle, and a spring motor removably secured to the outer needle. The introducer needle and the guide wire are inserted into a patient's vein and the spring motor releases the outer needle into the vein after the introducer needle and the guide wire are properly placed within the patient. The introducer needle, the guide wire, and the spring motor are removed from the patient after the outer needle is in place within the vein. The best use of this needle would be in conjunction with an ultrasound device which could see the vein and guide the introducer needle into the vein.

Other objects, features, and advantages of the invention will be readily apparent from the following detailed description of a preferred embodiment thereof taken in conjunction with the drawings.

BRIEF DESCRIPTION OF THE DRAWINGS

For the purpose of illustrating the invention, there is shown in the accompanying drawings one form that is presently preferred; it being understood that the invention is not intended to be limited to the precise arrangements and instrumentalities shown.

FIG. 3 illustrates the introducer needle and guide wire of the present device being inserted into a patient's vein;

FIG. 4 illustrates the outer needle of the present invention being inserted into a patient's; and FIG. 5 illustrates the flow of blood through the outer needle of the present invention.

DETAILED DESCRIPTION OF THE PREFERRED EMBODIMENT

Figure 1:
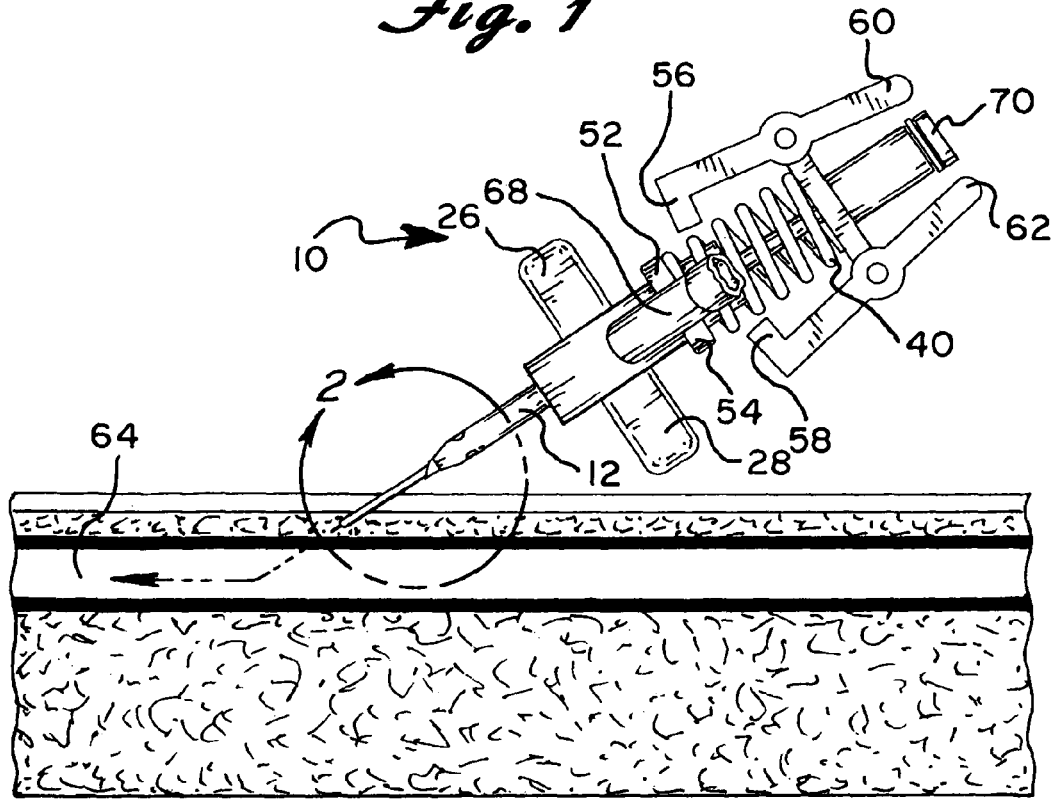
FIG. 1 illustrates the hemodialysis needle device of the present invention being used.

Referring now to the drawings in detail wherein like reference numerals have been used throughout the various figures to designate like elements, there is shown in FIG. 1 a hemodialysis needle constructed in accordance with principles of the present invention and designated generally as 10.

The hemodialysis needle and system of the present invention essentially includes a first large number 15 or number 17 gauge outer needle 12 having a conical tip 14 and a sidewall 16. The sidewall 16 includes a plurality of apertures 18 and 20, for example, located adjacent the conical tip or distal end 14. The proximal end 22 of the outer needle 12 is held within and secured to a support 24 as best shown in FIGS. 3, 4 and 5. Extending radially outwardly from the outer surface of the support 24 are a plurality of wing members such as shown at 26 and 28. As is known in the art, the primary purpose of the wing members 26 and 28 is to provide a means to tape the assembly to a patient's arm during dialysis to prevent it from moving after the needle 12 is in place.

Figure 2:
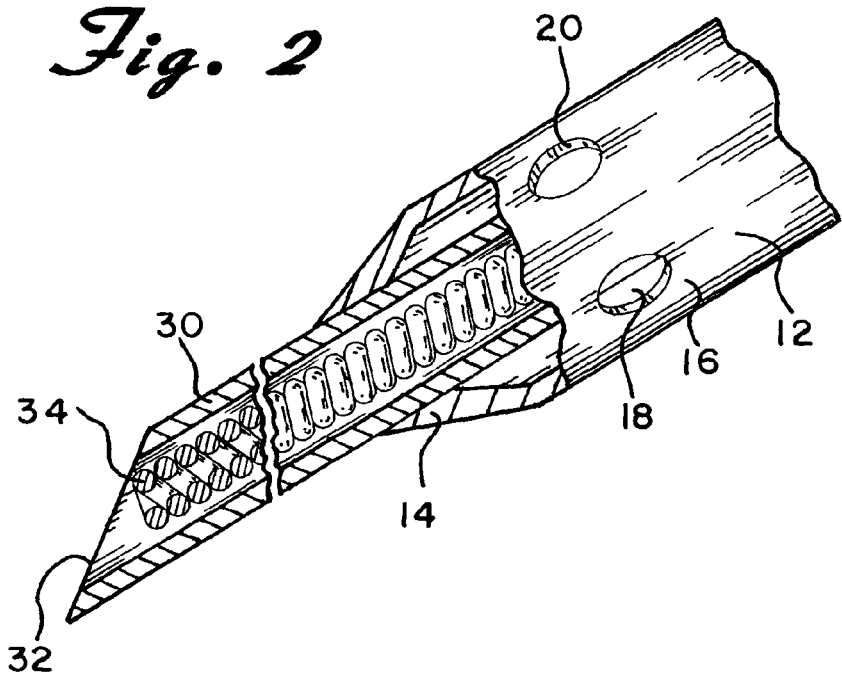
FIG. 2 is an enlarged view, shown partly in cross-sectional of the hemodialysis needle device taken through line 2-2 of FIG. 1.

A second, introducer needle 30 is located within the outer needle 12 and is axially moveable relative thereto. It is advantageous to have the introducer needle 30 as small as possible such as number 21 or 22 gauge. This will make it easier to access the vein and more importantly it will increase the peripheral radial blood flow. The forward distal end of the introducer needle 30 is tapered in the known manner as shown at 32. A guide wire assembly 34 is located within the introducer needle 30 (See FIG. 2) and, accordingly, also within the outer needle 12 and is also axially moveable relative thereto. A spring motor assembly 36 is attached to the needles in a manner to be described hereinafter.

The spring motor assembly 36 is comprised of the rear end 38 of the support 24, a compression spring 40 and a pair of levers 42 and 44. The levers 42 and 44 are pivoted at about their center points 46 and 48 to an intermediate member 50 that is secured to the rear end of the introducer needle 30 so as to be moveable therewith. Extending radially outwardly from the rear end 38 of the support 24 are a pair of flanges such as shown at 52 and 54. These flanges 52 and 54 need not be distinct separate elements but may be a single circular flange that surrounds the rear end 38 of the support 24.

As shown most clearly in FIGS. 3 and 4, the compression spring surrounds a part of the rear end 38 of the support 24 and is maintained in position between the flanges 52 and 54 at one end and the intermediate member 50 at the other end. The forward ends of the levers 42 and 44 include inwardly extending pawls 56 and 58 that are adapted to engage the forward surfaces of the flanges 52 and 54 as shown in FIG. 3. On the other hand, the rearward ends of the levers 42 and 44 include handles 60 and 62.

As should now be readily apparent from viewing FIGS. 3 and 4, with the spring 40 compressed, the pawls 56 and 58 engage the flanges 52 and 54. The engagement of the pawls 56 and 58 with the flanges 52 and 54 maintains the compression of the spring 40 and the pawls remain in place due simply to the frictional forces involved. In this position, the support 24 is close to the levers 42 and 44 and the handles 60 and 62. When the handles 60 and 62, however, are squeezed together (moved toward each other) the pawls 56 and 58 disengage themselves from the flanges 52 and 54 and the support 24 moves away from the intermediate member 50 by the force of the spring 40. The movement of the support 24 also, of course, carries with it the outer needle 12 as shown in FIG. 4.

In the arrangement of the spring motor means 36 of FIGS. 3 and 4, the support 24 and outer needle 12 can move freely under the force of the spring 40. In some situations, however, it may be advantageous to control the movement of the needle 12 to prevent a sudden jerking of the same during release. It may, therefore, be desirable to employ a damper device to the system.

In order to use the needle assembly 10 of the present invention, the introducer needle 30 is first inserted into a vein 64 of a patient's arm in the known manner. (See FIG. 1.) Thereafter, the guide wire 34 is inserted, also in the known manner. Once the introducer needle 30 and guide wire 34 are properly placed, the outer needle 12 is then guided toward the patient's arm by the needle 30 and the guide wire 34. At this point, the handles 60 and 62 are held and depressed thereby activating the spring motor 36 which moves the outer needle 12 to the left as viewed in FIG. 4 and into the patient. At all times, the outer needle 12 is being guided by the introducer needle and guide wire 34.

Once the outer needle 12 is in place, the support 24 can be taped to the patient's arm through the use of the wings 26 and 28 and the spring motor 36, introducer needle 30, and guide wire 34 can be completely withdrawn so that blood 66 flows through the outer needle 12 and through the channel 68 leading to the dialysis tubing. (See FIG. 5.) Of course, and is well known in the art, the septum seal 70 located at the end of the outer needle 12, remains in place 36 in order to prevent blood from flowing therethrough.

The use of a very small needle makes the procedure less painful and easier to find a vein. The guide wire leads the larger needle into the vein properly and with a minimum of trauma to the patient. The plurality of apertures aids in balancing and controlling the blood flow. The peripheral radial flow tends to center the needle by pushing the vein walls away from the needle.

The present invention may be embodied in other specific forms without departing from the spirit or essential attributes thereof and accordingly, reference should be made to the appended claims rather than to the foregoing specification as indicating the scope of the invention.

We claim:

1. A hemodialysis needle comprising:
    a first outer needle having a conical tip and a sidewall, said sidewall having a plurality of apertures located adjacent said tip;
    a second introducer needle located within said outer needle;
    a guide wire located within said introducer needle; and
    a spring motor removably secured to said outer needle;
    wherein said introducer needle and said guide wire are insertable into a patient's vein and said spring motor releases said outer needle into the vein after said introducer needle and said guide wire are properly placed within the patient;
    wherein said spring motor includes at least one lever pivotally attached to said introducer needle and movable therewith;
    wherein said lever includes a pawl and said outer needle carries a flange engageable by said pawl;
    wherein said spring motor drives said outer needle forwardly when said lever is depressed disengaging said pawl from said flange; and
    wherein said lever is accessible so that it can be manually depressed by a person in order to disengage said pawl.

2. The hemodialysis needle of claim 1 wherein said introducer needle, said guide wire, and said spring motor are removed from the patient after said outer needle is in place within the vein.

3. The hemodialysis needle of claim 1 further including a holder for securing said needles together.

4. The hemodialysis needle of claim 1, wherein said outer needle carries a pair of wings that prevent the outer needle from moving when it is taped to a patient's arm after it is positioned in a vein.

5. The hemodialysis needle of claim 1 wherein said outer needle carries a pair of wings that prevents the outer needle from moving when it is taped to a patient's arm after it is positioned in a vein.

6. A hemodialysis treatment method comprising the steps of:
    providing a first outer needle having a conical tip and a sidewall, said sidewall having a plurality of apertures located adjacent said tip; a second introducer needle located within said first needle; a guide wire located within said introducer needle; and a spring motor attached to said outer needle;
    inserting said introducer needle and said guide wire into a patient's vein;
    activating said spring motor wherein said outer needle is released and moved forwardly by said spring motor to follows said introducer needle and said guide wire into said vein; and
    withdrawing said introducer needle, said guide wire, and said spring motor from the patient.

* * * * *